United States Patent [19]

Beeley et al.

[11] Patent Number: 4,840,967
[45] Date of Patent: Jun. 20, 1989

[54] CARBAMATE OR UREA DERIVATIVES, THEIR PREPARATION AND PHARMACEUTICAL COMPOSITIONS COMPRISING THEM

[75] Inventors: Nigel Beeley, Combs la Ville; Gérard Cremer, Morangis, both of France

[73] Assignee: Synthelabo, Paris, France

[21] Appl. No.: 70,580

[22] Filed: Jul. 7, 1987

[30] Foreign Application Priority Data

Jul. 8, 1986 [FR] France ............................ 86 09887

[51] Int. Cl.⁴ ............... C07C 149/437; A61K 31/17; A61K 31/27
[52] U.S. Cl. .................................. 514/466; 514/522; 514/533; 514/539; 514/595; 514/596; 549/441; 558/417; 560/9; 560/10; 560/18; 564/47; 564/53; 564/54; 564/56
[58] Field of Search ............... 560/9, 10, 18; 564/47, 564/53, 54, 56; 558/412, 414, 417; 549/441; 514/466, 522, 533, 539, 595, 596

Primary Examiner—Michael L. Shippen
Attorney, Agent, or Firm—Fleit, Jacobson, Cohn, Price, Holman & Stern

[57] ABSTRACT

A compound which is a carbamate or urea derivative of general formula (I)

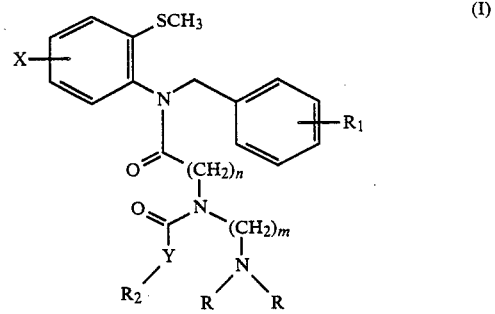

wherein
X is hydrogen, halogen or methylthio,
Y is oxygen or $$-\overset{|}{N}H,$$

R is $C_1$–$C_4$ alkyl,
$R_1$ is hydrogen, one or two halogen atoms or trifluoromethyl groups, a methyl group, a methoxy group, a cyano group, a nitro group, a methoxycarbonyl group, a methylenedioxy group linked to two adjacent carbon atoms of the benzene ring to which it is attached, or a fused benzo group forming an α-naphthyl or β-naphthyl group with the benzene ring to which it is attached,
$R_2$ is a linear or branched $C_1$–$C_8$ alkyl or alkenyl group optionally substituted with halogen atoms or a methoxy group, a cyclopropylmethyl group, or a phenyl group optionally substituted with one or two halogen atoms or methyl groups,
n is 1 or 2, and
m is 2 or 3, or an addition salt thereof with a pharmacologically acceptable acid is pharmacologically active as a calcium antagonist.

4 Claims, No Drawings

CARBAMATE OR UREA DERIVATIVES, THEIR PREPARATION AND PHARMACEUTICAL COMPOSITIONS COMPRISING THEM

The invention relates to novel carbamate and urea derivatives and their acid addition salts which are pharmacologically active as calcium antagonists.

According to the invention there is provided a compound which is a carbamate or urea derivative of general formula (I)

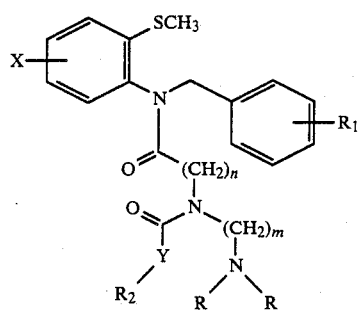

wherein
X is hydrogen, halogen or methylthio,
Y is oxygen or

R is $C_1$–$C_4$ alkyl,
$R_1$ is hydrogen, one or two halogen atoms or trifluoromethyl groups, a methyl group, a methoxy group, a cyano group, a nitro group, a methoxycarbonyl group, a methylenedioxy group linked to two adjacent carbon atoms of the benzene ring to which it is attached, or a fused benzo group forming an α-naphthyl or β-naphthyl group with the benzene ring to which it is attached,
$R_2$ is a linear or branched $C_1$–$C_8$ alkyl or alkenyl group optionally substituted with halogen atoms or a methoxy group, a cyclopropylmethyl group, or a phenyl group optionally substituted with one or two halogen atoms or methyl groups,
n is 1 or 2, and
m is 2 or 3, or an addition salt thereof with a pharmacologically acceptable acid.

The compounds of the invention can thus be presented in the states of free bases, or as addition salts with pharmacologically acceptable acids.

The preferred compounds are those of formula (I) in which n and m are each 2 and Y is an oxygen atom and their acid addition salts.

The compounds of the invention may be prepared, for example, by the process illustrated by the scheme on the following page.

In this process a 2-methylthiobenzenamine of formula (II) (in which X is as defined above) is condensed with a benzaldehyde of formula (III) (in which $R_1$ is as defined above), suitably in a solvent such as benzene under reflux, and preferably in the presence of para-toluenesulphonic acid, to provide an imine of formula (IV) which is then hydrogenated, for example by means of sodium cyanoborohydride, suitably in a solvent such as methanol and preferably at room temperature. The amine of formula (V) thereby obtained is reacted with an acid chlorine of formula (VI) (in which n is as defined above), suitably in a solvent such as ethyl ether and preferably at room temperature and in the presence of a base such as potassium carbonate.

SCHEME

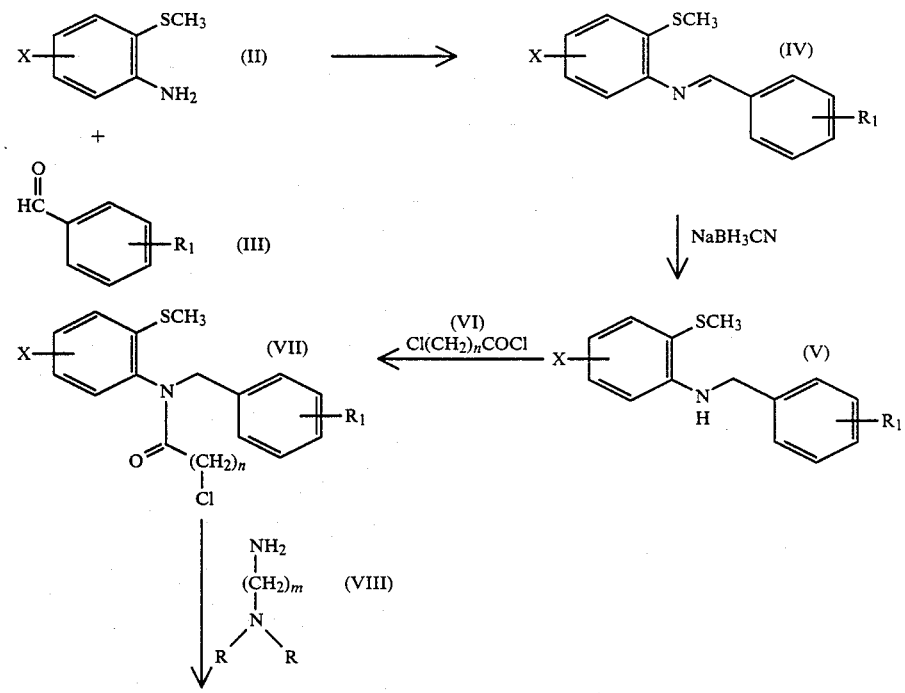

-continued
SCHEME

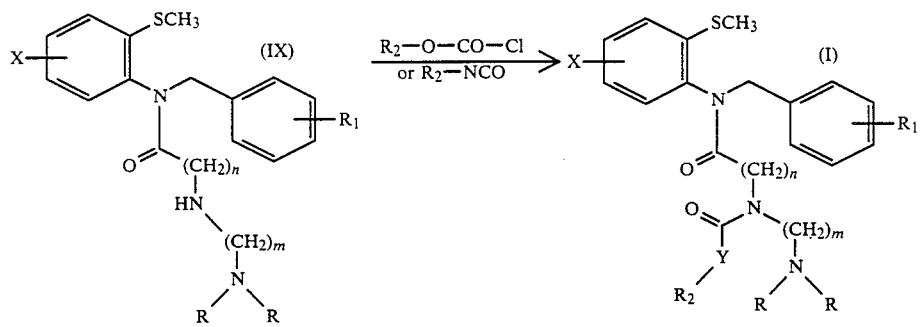

The chloride of formula (VII) thereby obtained is reacted with a diamine of formula (VIII) (in which R and m are as defined above), suitably in a solvent such as dimethylformamide and preferably at room temperature and in the presence of potassium iodide, to provide a compound of formula (IX) which is reacted with, when Y is to be oxygen, a chloroformate of formula $R_2$—O—CO—Cl (in which $R_2$ is as defined above), suitably in a solvent such as ethyl ether and preferably at room temperature and in the presence of a strong base such as sodium hydroxide, or with, when Y is to be =NH, an isocyanate of formula $R_2$—NCO (in which $R_2$ is as defined above), suitably in a solvent such as dichloromethane and preferably at room temperature, to provide a compound of formula (I). The compound of formula (I) can be converted, if desired, into an addition salt with a pharmacologically acceptable acid in manner known per se.

The following Example describes in detail a procedure for preparing the compounds of the invention.

The Table which follows the Example illustrates the structures and physical properties of some other compounds. The structures of the compounds thus described were confirmed by microanalyses and IR and NMR spectra.

EXAMPLE
2-Methylpropyl [2-(dimethylamino)ethyl][2-{[2-(methylthio)-phenyl][(3-trifluoromethylphenyl)methyl]amino}-2-]oxoethyl-carbamate 1. 2-(Methylthio)-N-{[3-(trifluoromethyl)phenyl]-methylene}benzenamine.

A mixture of 25 g (0.174 mole) of 2-methylthiobenzenamine and 25.06 ml (0.174 mole) of 3-trifluormethylbenzaldehyde in 250 ml of benzene is heated under reflux in the presence of 0.3 g of para-toluenesulphonic acid for 1 hour, the water formed being removed by means of a Dean and Stark apparatus.

The benzene is evaporated off and the oily residue used without further treatment in the following stage.

2. 2-(Methylthio)-N-{[3-(trifluoromethyl)phenyl]-methyl}benzenamide.

The residue from the above stage is dissolved in 300 ml of methanol, and 13.15 g of sodium cyanobrorohydride are added gradually while the mixture is stirred.

When the reaction is complete, the pH is adjusted to 6 with acetic acid and the solvent is then driven off.

The residue is taken up with either and sodium bicarbonate and the organic phase is separated, dried and evaporated. The residue is distilled at 135° C. under approximately 13 Pa. 35.7 g of amine are collected.

3. 2-Chloro-N-[2-(methylthio)phenyl]-N-{[3-(trifluoromethyl)phenyl]methyl}acetamide.

A mixture of 10 g (0.0337 mole) of the amine prepared above, 5.35 ml (0.067 mole) of chloroacetyl chloride and 40 g of potassium carbonate in 250 ml of ether is stirred at room temperature for 5 hours.

The inorganic products are separated by filtration, the filtrate is washed with sodium bicarbonate and then with water, and the organic phase is dried and evaporated. There remain 12.57 g of residue which is used without further treatment in the following stage.

4. 2-[2-(Dimethylamino)ethyl]amino-N-[2-(methylthio)-phenyl]-N-{[3-(trifluoromethyl)phenyl]methyl}acetamide.

The residue from the above stage is dissolved in 150 ml of dimethylformamide, and 11.07 ml (0.1 mole) of N,N-dimethyl-1,2-ethylenediamine and a spatula-tipful of potassium iodide are added.

The mixture is stirred at room temperature overnight, the solvent then evaporated off, the residue taken up with sodium bicarbonate and ether and the ether phase separated, dried and evaporated. There remain 12.5 g of crude product which are used without further treatment in the following stage.

5. 2-Methylpropl [2-(dimethylamino)ethyl][2-{[2-(methylthio)phenyl][(3-trifluoromethylphenyl)methyl]-amino}-2-oxoethyl]carbamate.

3 g (0.007 mole) of the product of the above stage are dissolved in 50 ml of ether, 25 ml of water are added and then, while the pH is monitored, caustic soda is added until the pH is 12.5 to 13.

1.8 ml (0.014 mole) of isobutyl chloroformate are then added dropwise, the pH being maintained by adding sodium hydroxide.

Stirring is continued at room temperature for 10 minutes, and the organic phase is then separated, dried and evaporated. The residue is purified by chromatography on silica, eluting with a 99:1 mixture of methanol and ether. 2 g of pure base are finally collected. The oxalate is prepared by dissolving the base and a stoichiometric amount of acid in a minimum of ethanol, and isolating the salt which crystallizes.

Melting point: 133° C.

TABLE (I)

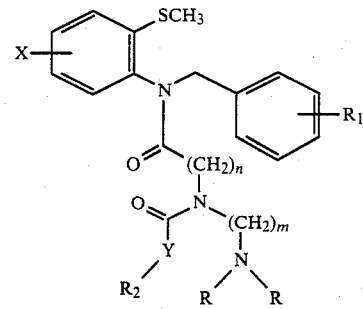

| N° | X | R₁ | Y | R₂ | R | n | m | Salt/base | M.p. (°C.) |
|---|---|---|---|---|---|---|---|---|---|
| 1 | H | H | O | iC₄H₉ | CH₃ | 1 | 2 | 46 | 134 |
| 2 | H | 2-Cl | O | iC₄H₉ | CH₃ | 1 | 2 | 46 | 137.5 |
| 3 | H | 3-Cl | O | iC₄H₉ | CH₃ | 1 | 2 | 46 | 126 |
| 4 | H | 4-F | O | iC₄H₉ | CH₃ | 1 | 2 | 46 | 142.5 |
| 5 | H | 2,6-Cl₂ | O | iC₄H₉ | CH₃ | 1 | 2 | 46 | 159 |
| 6 | H | 4-CH₃ | O | iC₄H₉ | CH₃ | 1 | 2 | 46 | 140 |
| 7 | H | 2-CN | O | iC₄H₉ | CH₃ | 1 | 2 | 46 | 155.5 |
| 8 | H | 4-CN | O | iC₄H₉ | CH₃ | 1 | 2 | 46 | 141.5 |
| 9 | H | 2-CF₃ | O | CH₃ | CH₃ | 1 | 2 | 46 | 141–143 |
| 10 | H | 2-CF₃ | O | iC₄H₉ | CH₃ | 1 | 2 | 46 | 135–136 |
| 11 | H | 3-CF₃ | O | CH₃ | CH₃ | 1 | 2 | 46 | 145 |
| 12 | H | 3-CF₃ | O | CH₂Cl₃ | CH₃ | 1 | 2 | 46 | 122–123 |
| 13 | H | 3-CF₃ | O | iC₄H₉ | CH₃ | 1 | 2 | 08 46 | 134–135 133 |
| 14 | H | 3-CF₃ | O | tC₄H₉ | CH₃ | 1 | 2 | 46 | 167–169 |
| 15 | H | 3-CF₃ | O | iC₅H₁₁ | CH₃ | 1 | 2 | 46 | 116–118 |
| 16 | H | 3-CF₃ | O | CH₂—tC₄H₉ | CH₃ | 1 | 2 | 46 | 145–146 |
| 17 | H | 3-CF₃ | O | CH(C₂H₅)₂ | CH₃ | 1 | 2 | 46 | 137–138 |
| 18 | H | 3-CF₃ | O | CH(CH₃)—iC₃H₇ | CH₃ | 1 | 2 | 46 | 134–135 |
| 19 | H | 3-CF₃ | O | CH₂—sC₄H₉ | CH₃ | 1 | 2 | 46 | 118–119 |
| 20 | H | 3-CF₃ | O | CH₂—cC₃H₅ | CH₃ | 1 | 2 | 46 | 125–126 |
| 21 | H | 3-OCH₂O—4 | O | CH₃ | CH₃ | 1 | 2 | 46 | 138 |
| 22 | H | 3-OCH₂O—4 | O | iC₄H₉ | CH₃ | 1 | 2 | 10 | 140–143 |
| 23 | H | α-C₁₀H₇ | O | iC₄H₉ | CH₃ | 1 | 2 | 46 | 153 |
| 24 | H | β-C₁₀H₇ | O | iC₄H₉ | CH₃ | 1 | 2 | 46 | 153 |
| 25 | H | 3-CF₃ | O | iC₄H₉ | nC₃H₇ | 1 | 2 | 46 | 78–79 |
| 26 | H | 3-OCH₂O—4 | O | CH₃ | nC₃H₇ | 1 | 2 | 46 | 116–118 |
| 27 | H | 3-CF₃ | O | CH₃ | nC₃H₇ | 1 | 2 | 46 | 80–82 |
| 28 | H | 3-OCH₂O—4 | O | iC₄H₉ | nC₃H₇ | 1 | 2 | 46 | 122–124 |
| 29 | H | 3-CF₃ | O | iC₄H₉ | CH₃ | 2 | 2 | 00 | Oil |
| 30 | H | 3-CF₃ | O | iC₄H₉ | CH₃ | 1 | 3 | 00 | Oil |
| 31 | H | 3,4-Cl₂ | O | iC₄H₉ | CH₃ | 1 | 2 | 46 | 137.5 |
| 32 | H | 2-OCH₃ | O | iC₄H₉ | CH₃ | 1 | 2 | 46 | 128–130 |
| 33 | H | 3-CF₃ 4-Cl | O | iC₄H₉ | CH₃ | 1 | 2 | 08 | 116 |
| 34 | H | 3-CF₃ 6-Cl | O | iC₄H₉ | CH₃ | 1 | 2 | 08 | 123–125 |
| 35 | H | 3-CF₃ 4-F | O | iC₄H₉ | CH₃ | 1 | 2 | 08 | 126–127 |
| 36 | H | 2-F | O | iC₄H₉ | CH₃ | 1 | 2 | 08 | 134–135 |
| 37 | H | 4-Cl | O | iC₄H₉ | CH₃ | 1 | 2 | 08 | 154–155 |
| 38 | H | 2,5-Cl₂ | O | iC₄H₉ | CH₃ | 1 | 2 | 08 | 156 |
| 39 | H | 2-Cl 6-F | O | iC₄H₉ | CH₃ | 1 | 2 | 46 | 148 |
| 40 | H | 2-NO₂ | O | iC₄H₉ | CH₃ | 1 | 2 | 46 | 149 |
| 41 | H | 2-CH₃ | O | iC₄H₉ | CH₃ | 1 | 2 | 46 | 123 |
| 42 | H | 4-CO₂CH₃ | O | iC₄H₉ | CH₃ | 1 | 2 | 46 | 156–157 |
| 43 | H | 4-CF₃ | O | iC₄H₉ | CH₃ | 1 | 2 | 08 | 134–136 |
| 44 | H | 3-CF₃ | O | CH(iC₃H₇)₂ | CH₃ | 1 | 2 | 46 | 133–134 |
| 45 | H | 3-CF₃ | O | CH(iC₃H₇)(C₂H₅) | CH₃ | 1 | 2 | 46 | 129–130 |
| 46 | H | 3-CF₃ | O | CH(iC₄H₉)(CH₃) | CH₃ | 1 | 2 | 46 | 117–118 |
| 47 | H | 4-CF₃ | O | CH₂C(CH₃)₃ | CH₃ | 1 | 2 | 10 | 122.5–124 |
| 48 | H | 3-CF₃ | O | iC₃H₇ | CH₃ | 1 | 2 | 46 | 134 |
| 49 | H | 3-CF₃ | O | CH₂C(CH₃):CH₂ | CH₃ | 1 | 2 | 46 | 128.5 |
| 50 | H | 3-CF₃ | O | CH₂CH:CH₂ | CH₃ | 1 | 2 | 46 | 143 |
| 51 | H | 4-CF₃ | O | iC₃H₇ | CH₃ | 1 | 2 | 46 | 142.5–143.5 |
| 52 | H | 4-CF₃ | O | CH₂C(CH₃):CH₂ | CH₃ | 1 | 2 | 46 | 142 |
| 53 | H | 4-CF₃ | O | CH₂CH₂—iC₃H₇ | CH₃ | 1 | 2 | 46 | amorphous |
| 54 | H | 2-OCH₃ | O | CH₃ | CH₃ | 1 | 2 | 46 | 96–97 |
| 55 | H | 4-CF₃ | O | tC₄H₉ | CH₃ | 1 | 2 | 46 | 147–147.5 |
| 56 | H | 4-CF₃ | O | CH₂—cC₃H₅ | CH₃ | 1 | 2 | 46 | 137.5–139.5 |
| 57 | H | 4-CF₃ | O | CH(iC₃H₇)(CH₃) | CH₃ | 1 | 2 | 46 | 142–143 |
| 58 | H | 3-CF₃ | O | CH(C₂H₅)(C₅H₁₁) | CH₃ | 1 | 2 | 00 | Oil |
| 59 | H | 3-CF₃ | O | CH(CH₃)(C₄H₉) | CH₃ | 1 | 2 | 00 | Oil |
| 60 | H | 3-CF₃ | O | CH₂CH₂OCH₃ | CH₃ | 1 | 2 | 46 | 126.5 |
| 61 | H | 3-CF₃ | O | CH(CH₃)(C₂H₅) | CH₃ | 1 | 2 | 46 | 144.5 |
| 62 | H | 3-CF₃ | O | CH(C₃H₇)(iC₃H₇) | CH₃ | 1 | 2 | 46 | 131.5 |
| 63 | H | 3-CF₃ | O | nC₈H₁₇ | CH₃ | 1 | 2 | 00 | Oil |
| 64 | 3-Cl | 4-Cl | O | iC₄H₉ | CH₃ | 1 | 2 | 46 | 86.5 |

TABLE-continued

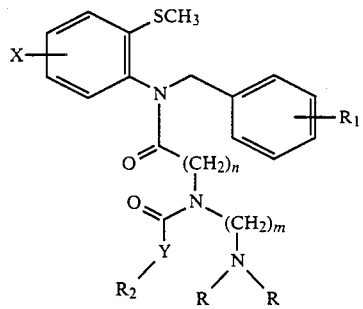
(I)

| N° | X | R₁ | Y | R₂ | R | n | m | Salt/base | M.p. (°C.) |
|---|---|---|---|---|---|---|---|---|---|
| 65 | 4-Cl | 4-CF₃ | O | iC₄H₉ | CH₃ | 1 | 2 | 46 | amorphous |
| 66 | 3-Cl | 4-F | O | iC₄H₉ | CH₃ | 1 | 2 | 46 | 120–121 |
| 67 | 3-Cl | 2-F | O | iC₄H₉ | CH₃ | 1 | 2 | 46 | 131–132 |
| 68 | 5-Cl | 4-CF₃ | O | iC₄H₉ | CH₃ | 1 | 2 | 46 | 144–145 |
| 69 | 6-SCH₃ | 4-CF₃ | O | iC₄H₉ | CH₃ | 1 | 2 | 46 | 152 |
| 70 | 4-Cl | 3-CF₃ | O | iC₄H₉ | CH₃ | 1 | 2 | 46 | 120 |
| 71 | H | 3-CF₃ | NH | nC₃H₇ | CH₃ | 1 | 2 | 46 | 118–119 |
| 72 | H | 3-CF₃ | NH | iC₃H₇ | CH₃ | 1 | 2 | 46 | 138–139 |
| 73 | H | 3-CF₃ | NH | nC₄H₉ | CH₃ | 1 | 2 | 46 | 126 (dec) |
| 74 | H | 3-CF₃ | NH | C₆H₅ | CH₃ | 1 | 2 | 46 | 132–133 |
| 75 | H | 3-CF₃ | NH | C₆H₄—F(2) | CH₃ | 1 | 2 | 00 | 126–127 |
|    |   |       |    |          |     |   |   | 08 | 160 (dec) |
|    |   |       |    |          |     |   |   | 46 | 162–163 |
| 76 | H | 3-CF₃ | NH | C₆H₄—F(2) | CH₃ | 1 | 3 | 46 | 146 |
| 77 | H | 3-CF₃ | NH | C₆H₄—F(2) | CH₃ | 2 | 2 | 46 | 168 |
| 78 | H | 4-CF₃ | NH | C₆H₃—CH₃(2)-F(5) | CH₃ | 1 | 2 | 46 | 143–144 |
| 79 | H | 4-CF₃ | NH | C₆H₃—CH₃(2)-Cl(6) | CH₃ | 1 | 2 | 46 | 143 |
| 80 | H | 4-CF₃ | NH | C₆H₃—F₂(2,6) | CH₃ | 1 | 2 | 46 | 171.5–172 |
| 81 | H | 4-CF₃ | NH | C₆H₃—Cl₂(2,6) | CH₃ | 1 | 2 | 46 | 159–160 |
| 82 | H | 4-CF₃ | NH | C₆H₄—F(2) | CH₃ | 1 | 2 | 08 | 162 |

Legend to the table

"R₁" column: α-C₁₀H₇ and β-C₁₀H₇ denote α-naphthyl and β-naphthyl radicals, respectively, formed by R₁ and the benzene ring to which it is attached.

"R₂" column: nC₃H₇, iC₃H₇, C₃H₅, nC₄H₉, iC₄H₉, tC₄H₉, sC₄H₉, iC₅H₁₁ and nC₈H₁₇ denote n-propyl, isopropyl, cyclopropyl, n-butyl, isobutyl, tert-butyl, sec-butyl, isopentyl and n-octyl radicals, respectively. C₆H₅, C₆H₄—Z(p) and C₆H₃—Z(p)-W(q) denote phenyl radicals, and phenyl radicals monosubstituted or disubstituted with Z and/or W at the p- and q-positions, respectively.

"Salt/base" column: 00, 08, 10 and 46 denote the free base, the fumarate, the hydrochloride and the oxalate, respectively.

The compounds of the invention were subjected to pharmacological trials which demonstrated their activity as a calcium antagonist.

The experimental protocol used is a variant of that of Godfrained and Kaba (Blockade or reversal of the contraction induced by calcium and adrenaline in depolarized arterial smooth muscle, Br. J. Pharmac., (1969) 36, 549–560).

The experiments were carried out on sectional lengths of rabbit thoracic aorta. The animals, "Fauves de Bourgogne" of average weight 1.5 kg, were sacrificed by cervical dislocation and exsanguination. The thoracic aorta was rapidly removed and placed in an oxygenated Krebs bicarbonate medium (95% $O_2$+5% $CO_2$).

Sectional lengths of aorta approximately 1 cm long were prepared and mounted in 20-ml organ cells containing oxygenated Krebs bicarbonate solution at pH 7.4 at 37° C. Two U-shaped metal hooks having the same length as the sectional lengths were introduced into the bore of the latter. One of the hooks was attached to the base of the cell and the other, connected to an isometric strain gauge (Grass FT03), enables the contractile responses of the sectional lengths of aorta to be recorded, via a continuous preamplifier (Grass 7P1), on a recording oscillograph (Grass 79B). This method has the advantage, compared with spiral- or ring-shaped preparations, of preserving more faithfully the structural integrity of the vessels and of recording only the radial components of the contractile responses, which represents the phenomenon which is of interest from a functional standpoint (regulation of the arterial blood pressure). An initial tension of 4 g was applied to the preparations.

Phenoxybenzamine (1 μM) and propranolol (1 μM) were added to the different Krebs media in order to eliminate the contractile responses linked to the activation of the vascular α- and β-adrenergic receptors.

After one hour's stabilization in Krebs medium, the tension applied to the aortas was reduced to 2 g, and then, after a 30-minute waiting period, the preparations were incubated for about ten minutes in a calcium-free Krebs bicarbonate solution in the presence of EDTA (200 μM) and propranolol (1 μM). This solution was then replaced by a calcium-free depolarizing (potassium-rich) Krebs medium containing propranolol (1 μM). After 5 minutes, a single 1 mM concentration of calcium was added to this solution and a 30-minute stabilization period was observed, this enabling the preparations to attain a stable contraction.

Cumulative doses of the test compounds were then administered every 30 minutes (the time generally needed for obtaining a stable condition) until there was complete disappearance of the contraction induced by 1 mM calcium, or alternatively until the concentration (30 μM) of test product was attained. At the end of the experiment, a supramaximal concentration of papaverine (300 μM) is administered in order to determine the maximum possible relaxation of each preparation.

The aboslute values (in grams) of the initial contraction (after 1 mM calcium chloride) and of the contraction after the different cumulative concentrations of vasodilatory compounds were obtained, for each preparation, by difference with the minimal contraction observed 30 minutes after the final addition of 300 μM papaverine. The percentage decrease in the contraction, relative to the contraction induced by 1 μM calcium, was calculated for each dose of compound and each preparation, and the mean $\overline{X}\pm SEM$ of the individual percentages is calculated. The mean values obtained (weighted by the reciprocal of the standard error of the mean) were analysed using a mathematical sigmoid curve model, and the molar concentration inducing 50% relaxation of the response to calcium ($EC_{50}$) was calculated.

For the compounds of the invention, the $EC_{50}$ values range from 0.6 μM to 30 μM.

The compounds of the invention can be used for the treatment of all diseases in which calcium antagonists can be used, such as angina pectoris, cardiac arrhythmia, hypertension, cardiomyopathy, myocardial protection of patients at risk of infarction or who have suffered an infarction, cardiac arrest, stroke, mania, migraine.

Other trials have shown that the compounds of the invention also inhibit platelet aggregation, and they may hence be used for the treatment of conditions which result therefrom.

Finally, trails performed on animals subjected to stress have shown that the compounds of the invention also have properties for combatting gastric or gastroduodenal ulcers.

The compounds of the invention can be presented in any form suitable for oral or parenteral administration, in combination with any suitable excipient, for example in the form of tablets, gelatin capsules, capsules, solutions for oral administration or injectable solutions.

The daily dosage can range from 30 to 600 mg orally and from 0.06 to 180 mg parenterally.

We claim:

1. A compound which is a carbamate or urea derivative of general formula (I)

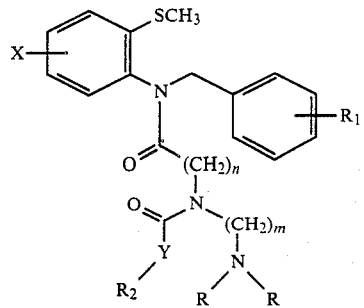

wherein
X is hydrogen, halogen or methylthio,
Y is oxygen or

R is $C_1-C_4$ alkyl,
$R_1$ is hydrogen, one or two halogen atoms or trifluoromethyl groups, a methyl group, a methoxy group, a cyano group, a nitro group, a methoxycarbonyl group, a methylenedioxy group linked to two adjacent carbon atoms of the benzene ring to which it is attached, or a fused benzo group forming an α-naphthyl or β-naphthyl group with the benzene ring to which it is attached,
$R_2$ is a linear or branched $C_1-C_8$ alkyl or alkenyl group optionally substituted with halogen atoms or a methoxy group, a cyclopropylmethyl group, or a phenyl group optionally substituted with one or two halogen atoms or methyl groups,
n is 1 or 2, and
m is 2 or 3, or an addition salt thereof with a pharmacologically acceptable acid.

2. A compound according to claim 1, wherein n and m are each 2, and Y is oxygen.

3. A compound according to claim 1, wherein X is hydrogen, $R_1$ is 3-trifluoromethyl, Y is oxygen, $R_2$ is isobutyl, R is methyl, n is 1 and m is 2.

4. A calcium antagonist pharmaceutical composition which comprises an effective amount of a compound as claimed in claim 1 in associated with a pharmacologically acceptable excipient.

* * * * *